United States Patent [19]

Katz et al.

[11] Patent Number: 4,783,656

[45] Date of Patent: * Nov. 8, 1988

[54] INTRA-ORAL CONTROL UNIT AND SYSTEM

[75] Inventors: Philip Katz, Princeton Junction, N.J.; Harold Schwartz, King of Prussia, Pa.

[73] Assignee: Thomas Jefferson University, Philadelphia, Pa.

[*] Notice: The portion of the term of this patent subsequent to Aug. 12, 2003 has been disclaimed.

[21] Appl. No.: 926,875

[22] Filed: Nov. 4, 1986

Related U.S. Application Data

[63] Continuation of Ser. No. 771,275, Aug. 30, 1985, abandoned, which is a continuation-in-part of Ser. No. 526,699, Aug. 26, 1983, Pat. No. 4,605,927.

[51] Int. Cl.$^4$ ............... H04B 1/034; G08B 21/00; H04Q 9/00
[52] U.S. Cl. .................. 340/825.190; 128/777; 340/407; 455/100
[58] Field of Search ........... 340/825.19, 825.69, 340/407; 128/777, 787, 421; 381/70; 455/100

[56] References Cited

U.S. PATENT DOCUMENTS

| | | | |
|---|---|---|---|
| 3,297,021 | 1/1967 | Davis et al. | 128/777 |
| 3,524,932 | 8/1970 | Stucki | 128/777 |
| 4,157,540 | 6/1979 | Oros | 455/100 |
| 4,473,905 | 9/1984 | Katz et al. | 381/70 |
| 4,502,151 | 2/1985 | Castle et al. | 381/70 |
| 4,550,427 | 10/1985 | Katz et al. | 381/70 |
| 4,605,927 | 8/1986 | Katz et al. | 340/825.19 |
| 4,629,424 | 12/1986 | Lauks et al. | 455/100 |

OTHER PUBLICATIONS

Burnett, P. and Sutton, R. A.: "A Portable Electronic 'Calling Device' as an Aid to Weaning Ventilator-Dependent Tetraplegic Patients from Intermittent Positive Pressure Ventilation", Paraplegia, 17:563-566, 1979.

Cloran, A. J.; Lotz, J. W.; Campbell, H. D.; Howard D. Campbell; Wiechers, D. O.; "Oral Telescoping Orthosis: An Aid to Functional Rehabilitation of Quadriplegic Patients." J.A.D.A., vol. 100, pp. 876-879, Jun. 1980.

Efthimiou, M. A.; Gordon, W. A.; Sell, G. H.; and Stratford, C.: "Electronic Assistive Devices: Their Impact on the Quality of Life of High Level Quadriplegic Persons" Arch. Phys. Med. Rehabil., vol. 62, pp. 131-134, Mar., 1981.

Garrison, J. H.; "Emergency Signaling for a Person with Quadriplegia and Extraordinary Respiratory Risk", Arch. Phys. Med. Rehabil. vol. 63, pp. 180-181, Apr., 1982.

Green, R.: "The Current Status of and Future Considerations for Environmental Control Systems", Bull. Prost. Res., pp. 310-325, 1974.

Guittet, J.; Kwee, H. H.; Quetin, N.; Yclon, J.: "The Spartacus Telethesis: Manipulator Control Studies." Bull. Prosth. Res., BPR 10-32, pp. 69-105, Fall, 1979.

(List continued on next page.)

*Primary Examiner*—Donald J. Yusko
*Attorney, Agent, or Firm*—Woodcock Washburn Kurtz Mackiewicz & Norris

[57] ABSTRACT

A system for quadriplegics and for others having less than full use of their limbs for controlling the environment is disclosed. The system includes an intra-oral lingually operated switch located on a dental appliance. The switch activates an intra-oral power supply and intra-oral FM transmitter which directs control signals from the inside of the oral cavity to an external FM receiver. A controller responsive to the receiver generates output signals for operating call devices, and for controlling various appliances such as televisions, lights, bed position, etc. In one embodiment, a delay circuit is interposed between the intra-oral switch and the power supply such that inadvertent closure of the switch with the tongue does not cause undue power drain. An improved FM transmitter circuit is also disclosed which has low power drain, has low mass and temperature sensitivity and is not directional.

6 Claims, 3 Drawing Sheets

OTHER PUBLICATIONS

Jones, R. D.; Hooper, R. H.; Armstrong, D. I.; Fisher, C. J.; Tait, J. J.: "Microprocessor-Based Multi-Patient Environmental-Control System for a Spinal Injuries Unit" Med. & Biol. Eng. & Comput., 18:607–616, Sep., 1980.

Katz, P.: Schwartz, H. L.; Brenman, H. S. and Lowry, L. D.: "A Clinical Device for Revocalization of the Laryngectomized Patient", IEEE Fon. Eng. Health Care, pp. 318–320, Sep., 1981.

Newhouse, V. L.; Ho, C. T.; and Pairitz, J. F.: "Voice Operated Transducer for the Disabled", J. Clin. Eng., vol. 5, No. 2, Apr.–Jun., 1980, pp. 139–144.

Parish, J. G.: "A Study of the Use of Electronic Environmental Control Systems by Severely Paralyzed Patients", Paraplegia 17, 147–152, 1979–80.

Powner, D. J.: "Call Systems for Quadriplegic Patients" Critical Care Medicine, 312–313, Fall, 1980.

Schmeisser, G. and Seamone W.: "An Assistive Equipment Controller for Quadriplegics", John Hopkins Med. Journ., 145:84–88, 1979.

Schwartz, H. L.; Westerhouse, J.; Zafran, J. and Zayon, G. "A Study of Tongue Movements Using Dynamic Palatography" Proc. 29th ACEMB, 1976.

Schwartz, H. L. and Taylor, D. R.: "The Observation of Tongue Movements Using Dynamic Palatography" Proc. 30th ACEMB, 1977.

Schwartz, H. L. and Katz, P.: "Biofeedback Device for Tongue Placement Evaluation/Therapy." Proc. 33rd ACEMB, 1980.

Sell, G. H.; Stratford, C. D.; Zimmerman, M. E.; Youdin, M. Milner, D.: "Environmental and Typewriter Control Systems for High-Level Quadriplegic patients: Evaluation and Prescription" Arch. Phys. Med. Rehabil. 60:246–252, 1979.

Shannon, D. A.; Staewen, W. S.; Miller, J. T.; Cohen, B. S.: "Morse-Code-Controlled Computer Aid for the Nonvocal Quadriplegic, Med. Instr., vol. 15, No. 5, 341–343, Sep.–Oct., 1981.

Steadman, J. W.; Ferris, C. D.; and Rhodine, C. N.: "Prosthetic Communication Device" Arch. Phys. Med. Rehabil. vol. 61, pp. 93–97, Feb., 1980.

Tunstall, M. E. and Bolton, M. P.: "Simple Alarm for Quadriplegic Patients" Anaesthesia, 1977, vol. 32, pp. 177–178.

Young, J. S. and Northup, N. E.: "Statistical Information Pertaining to Some of the Most Commonly Asked Questions About SCI" National Spinal Cord Injury Data Research Center, Phoenix, AZ, Aug., 1979.

Zimmerman, M. D.: "Technology for the Handicapped" Mach. Design, pp. 38–43 Apr., 1982.

Rinard, G.; Rugg, D.: "An Ocular Control Device for Use by the Severely Handicapped" Conference System & Devices for Disabled, Boston, Jun., 1976.

Rusk, H. A.: "Evaluation of Electronic Self-Help Devices for Severely Disabled Patients", Bulletin of Prosthetics Research BPR 10-33, vol. 17, No. 1 Spring, 1980.

Burnham, L. and Werner G.: "The High-Level Tetraplegic; Psychological Survival and Adjusgment" Paraplegia 16, 1984–192, 1978–79.

Warren, C. G.; Wilson, S. and Terami, B.: "Electric Bed Control: Mechanical Assist for Quadriplegic Patients" Arch. Phys. Med. Rehabil vol. 55, 560–61, 1974.

Peizer, E.; Lorenze, E. J. and Dixon, M.: "Environmental Controls to Promote Independence in Severely Disabled Elderly Persons", Med. Instrumentation, vol. 16, No. 3, May–Jun., 1982.

Rogers, J. C.; and Figone, J. J.: "Traumatic Quadriplegia: Follow-Up Study of Self-Care Skills", Arch. Phys. Med. Rehabil: vol. 61, pp. 316–321, Jul., 1980.

INTRA-ORAL CONTROL UNIT AND SYSTEM

BACKGROUND OF THE INVENTION

This is a continuation of application Ser. No. 771,275, filed Aug. 30, 1985, now abandoned, which in turn is a continuation-in-part of application Ser. No. 526,699, filed Aug. 26, 1983, now U.S. Pat. No. 4,605,927.

The present invention relates in general to an intra-oral control unit and system and, in particular it relates to an intra-oral control unit and system for use in controlling the environment of persons having less than full use of their limbs and which is especially useful for quadriplegics.

An increasing number of patients with high-level spinal cord injuries resulting in quadriplegia are being treated. The quadriplegic condition can result from many causes such as trauma which is due to vehicular and diving accidents, gunshot wounds, etc., spinal tumors or congenital malformations of the vertebrae, bacterial and viral infections, and neuromuscular disorders such as muscular dystrophy and multiple sclerosis. Many quadriplegic patients have a serious problem in communication during the early phase of their hospital stay. This problem with communication is a result of being ventilator-dependent, or of having minimal voice control. The treatment of the quadriplegic patient is first concerned with the survival of the patient and this usually occurs in an intensive care unit. At this stage of treatment, the patient has either significantly compromised respiratory parameters or is mute due to ventilator dependence. Many such patients have no mobility of the head due to traction. Many patients with cervical lesions remain in permanent traction for four to six weeks during which time the head is held in a position perpendicular to the surface of the bed. Because of this degree of restriction and the isolation in an intensive care unit, it is vital that the patient be provided with a device to gain the attention of the clinician.

Many types of patient-operated call systems have been used for such patients and are described in the literature. Such call devices may generally be categorized as sip/puff mechanisms, mouth wands and physiological response devices such as eye blink detectors and movement activated switches. All of these devices suffer from disadvantages associated with their use. The use of an air activated switch, such as a sip/puff device, is often not possible due to significantly compromised respiratory parameters or ventilator dependence. Even when sufficient air supply exists, the patient's speech may tend to be unreliable in volume and pronunciation. Thus, voice actuated devices are also unreliable. While the use of a mouth wand or stick is feasible, its communicative properties are slow and tiring to the user. Physiological response devices, such as eye blink detectors and movement activated switches tend to be unreliable. Physiological response devices falling into this category, in addition to eye blink detectors, include devices for the detection of head or shoulder motions, devices for the detection of myoelectric signals from the muscles around the head and neck, devices for the detection of eyebrow motion, jaw or chin movement and tongue contact. Utilization of such devices including those dependent upon residual arm, shoulder or leg movement of the patient for activation of physiological response devices is undesirable because such devices tend to produce inconsistent results and must be customized to each patient.

The present invention seeks to overcome the aforementioned disadvantages by providing a call device which capitalizes upon the fact that one voluntary function which is usually intact in a quadriplegic patient is the lingual function. Since the control of the tongue is vital for the primary acts of swallowing and eating, its capability is always evaluated early in the patient's treatment and reinforced if necessary. Devices for environmental control by a quadriplegic utilizing the tongue are known. One such system has been described for use by a quadriplegic which includes the placement of an electrical contact below the external lower lip which is activated by the tongue of a quadriplegic in order to sound an alarm. See M. E. Tunstall and M. P. Bolten, "Simple Alarm for Quadriplegic Patients", Vol. 32, *Anesthesia*, pages 177–178, 1977. Such a device suffers severe disadvantages.

After the initial therapeutic phase in an intensive care unit, the quadriplegic patient has usually progressed to the point where, in addition to the need for calling someone, it is desirable to control surrounding devices. Devices are known which control various pieces of equipment used by quadriplegics such as alarms, wheelchairs, computers, telephones and typewriters. In this category, devices are known which utilize head movements, sip/puff switches, vocal commands and finger or thumb movements for the activation of environmental control units. Such techniques suffer from the disadvantages referred to above.

It is an object of the present invention to provide an environmental control unit and system which obviates the aforementioned disadvantages.

It is a further object of the present invention to provide an environmental control unit and system which may be used as a call device and which alternatively may also be used to control external equipment and appliances.

It is a still further object of the present invention to provide such a unit and system which is activated by the tongue but which is mounted internally.

It is still another object of the present invention to provide an environmental control system capable of monitoring a plurality of quadriplegic patients simultaneously.

It is a still further object of the present invention to provide a system which is useful in any application in which an individual is required to control his external environment but is unable to use his limbs.

SUMMARY OF THE INVENTION

The foregoing objectives are achieved in accordance with the present invention by the provision of an environmental control unit which includes an intra-oral, lingually operated switching means, an intra-oral power supply and an intra-oral transmitter responsive to the switching means and to the power supply for transmitting control signals upon lingual activation of the switching means. In accordance with an important aspect of the present invention, the intra-oral switching means comprises a control means including a timing portion, a demand power supply, a first oscillating means, responsive to the demand power supply, for generating a first low frequency modulating signal and a transmitter enabling means for outputting the modulating signal for a predetermined time whenever the switching means is activated. The transmitter is responsive to the modulating signal and generates control signals which are transmitted from the intra-oral cavity.

In accordance with an important aspect of the present invention, the environmental control unit mentioned above is part of an overall environmental control system which includes an external FM receiver and a controller responsive to that receiver. The controller may be utilized to operate a call device in one embodiment. In still another embodiment of the present invention, the controller may be utilized to provide environmental control such as, for example, the operation of servo mechanisms to raise and lower a bed position, to increase or decrease room temperature, to change television volume, channel, etc.

In accordance with still another embodiment of the present invention, a plurality of patients are each provided with an environmental control unit which is monitored by a single FM receiver. The modulated signal transmitted from each patient differs from that of other patients and thus a plurality of patients may be monitored in a simple and efficient manner.

An intra-oral lingually operated switch which comprises a part of the switching means of the present invention is known. One such switch is disclosed in copending application Ser. No. 438,376 filed Nov. 1, 1982, now U.S. Pat. No. 4,550,427, by Philip Katz, Henry S. Brenman, Louis D. Lowry and Harold Schwartz entitled "Artificial Larynx", which application is incorporated herein by reference. In that application, an intra-oral switch is disclosed which is placed upon a dental appliance, the switch being closed when the tongue bridges electrical contacts on the appliance. In U.S. Pat. No. 4,550,427, however, the output of the device disclosed therein is acoustic rather than electromagnetic. While the intra-oral cavity is a satisfactory environment from which to transmit acoustic energy, this cavity represents a severely hostile environment from which to transmit electromagnetic energy of the type envisioned in the present application.

Transmission of electrical energy from the intra-oral cavity imposes severe design constraints upon the realization of both the transmitter and power supply of the present invention. First, the intra-oral cavity represents only a small volume in which to house the components required for the present invention. Second, the absorbance of the surrounding tissue of the intra-oral cavity makes signal transmission from it a difficult task. Thirdly, the temperature of an intra-oral transmitter may vary substantially from that of body temperature depending upon the temperature of the air passing through the cavity. Since the carrier frequency of the transmitter oscillator is often temperature-dependent many transmitter oscillator designs are simply inapplicable. Because of these constraints, both the intra-oral switching means and transmitter of the present invention must be small in size and have low power consumption. The transmitter must also be one which is not directional such that movement of the transmitter with respect to the receiver causes a diminution in signal. Still further, the transmitter must be one which is not temperature dependent and which is not mass sensitive, i.e., does not suffer a degradation in signal upon movement of the patient's tongue.

In the development of the intra-oral transmitter of the present invention and in an attempt to avoid these constraints various approaches were tried. Amplitude modulation, as opposed to frequency modulation, was first employed. It was found that intra-oral transmitters employing amplitude modulation were directional, had low sensitivity, and high power drain. It was also found that such transmitters had a size which is unduly large.

Tunnel diode transmitters, both FM and AM were next employed. It was found that such transmitters did not have suitable frequency stability. FM transmitters were also tried having LC oscillator circuits of the Colpitts type and also of the Hartley type. It was found that these transmitters had high power consumption and were both mass and temperature sensitive. Initial attempts to employ transmitters having crystal oscillators were unsuccessful. It was found that such transmitters were unduly large, were mass sensitive and were difficult to tune. Designs employing crystal controlled varacter transmitters were also attempted, but it was found that these, too, were unduly large and had excessive power drain. Next, an FM transmitter which employed a modified Colpitts oscillator was designed and employed which was suitable for reliable transmission from the intra-oral cavity. This transmitter is set forth and described in detail in the parent application to the present application. Further work has now resulted in the transmitter of the present invention which has proven more reliable than that previously disclosed.

Thus, in addition to a general concept set forth above, the present invention is also directed to a specific intra-oral FM transmitter which does not suffer from the aforementioned adverse temperature dependence, mass sensitivity, and directionality, which is sufficiently miniaturized so as to be located intra-orally and which has sufficiently low power drain as to permit use over extended periods of time and which is suitably sealed to function in the hostile environment.

The transmitter and control circuitry set forth in the parent application have also been found to require power from the on-board power supply as long as the lingual contact is depressed. Such a design is not optimum because the life of the power supply is not maximized. The present invention includes a novel intra-oral switching means having control circuitry and a demand power supply which enables the transmitter only when required by the patient thus greatly extending battery life.

BRIEF DESCRIPTION OF THE DRAWINGS

The present invention will be more fully understood by reference to the accompanying drawings in which.

DETAILED DESCRIPTION OF THE PREFERRED EMBODIMENT

Figure 1:
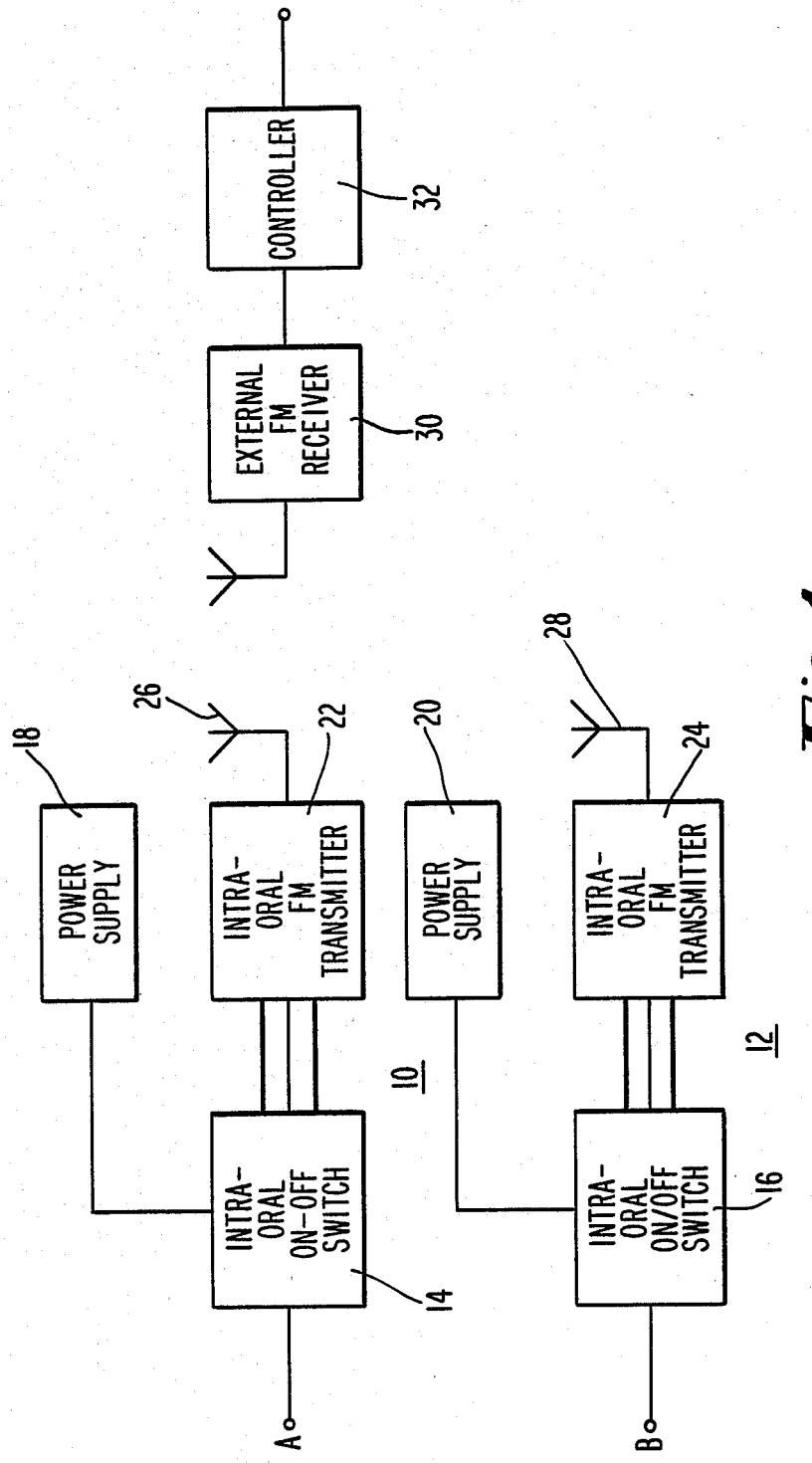
FIG. 1 is a block diagram of an environmental control system of the present invention.

Referring now to FIG. 1 a block diagram of the environmental control unit and system of the present invention is disclosed. In the embodiment shown in FIG. 1, two environmental control units 10 and 12 are shown, the unit 10 being used by a first patient A and the unit 12 being utilized by a second patient B.

Each of the environmental control units 10 and 12 employs an intra-oral on/off switching means 14 and 16, respectively. Each of the environmental control units 10 and 12 also includes an on-board power supply 18 and 20, respectively. In accordance with the preferred embodiment of the present invention this power supply comprises batteries which may be of the lithium, silver oxide or nickel cadmium type, although 3 volt lithium batteries are particularly preferred. The intra-oral switching means 14 and 16 are preferably located on a conventional palatal denture or dental appliance. The body of the dental appliance is formed from conventional dental prosthetic materials, such as an acryli polymer, which is shaped to fit comfortably against the roof of the wearer's mouth. Located upon this prosthesis are contacts which are lingually activated. The contacts are preferably one or more pairs of Ag-AgCl contacts which may be bridged with the tongue or alternatively a sealed momentary switch which may be activated by the tongue. In the case of the Ag-AgCl contacts, the touching of such contacts by the tongue completes a ground path for activating an intra-oral FM transmitter 22, 24 located in each environmental control unit 10, 12. The output of the FM transmitter 22, 24 is connected to an antenna means 26, 28 from which emanates control signals for transmission outside the intra-oral cavity. Each FM transmitter 22, 24 employs the same carrier frequency, but with each having its own unique subcarrier frequency. The environmental control unit 10 is encapsulated with a suitable sealant such as medical grade silicone-type adhesive.

Each of the intra-oral environmental control units 10 and 12 referred to above are part of a single overall environmental control system for use with a plurality of patients. In addition to the intra-oral control units 10 and 12, this system includes an external FM receiver 30 which monitors a plurality of patients and an external controller 32. The FM receiver is tuned to receive FM carrier signals emanating from antennae 26, 28. This external FM receiver operates in the FM band.

The audio output of the FM receiver 30 is directed to the controller 32 which includes a plurality of phase-lock loop tone decoders each associated with the subcarrier frequency of the monitored patient. The output of the phase-lock loop tone decoders of controller 32 may be used to control a simple device such as a latching relay or lamp to summon a nurse, a stepper mechanism to change television channels, or a more sophisticated sequencer to control a remote control device.

Figure 2:
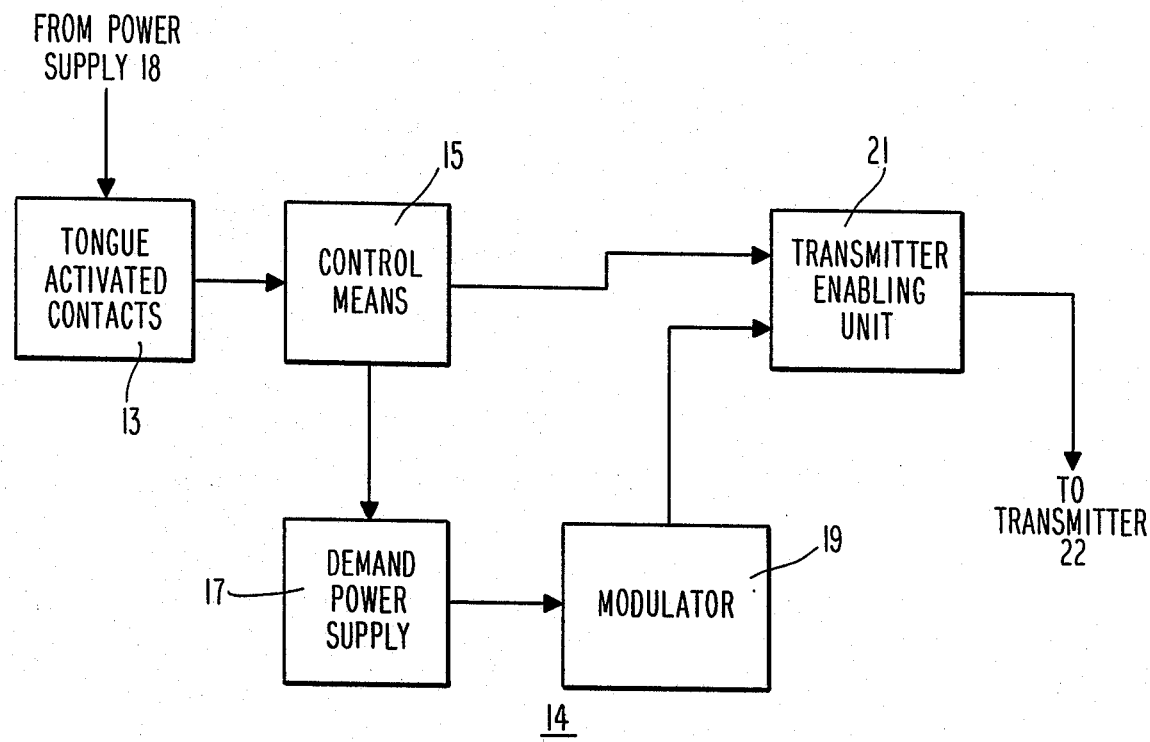
FIG. 2 is a block diagram of an intra-oral on/off switch of the type useful in connection with the system of FIG. 1.

Referring now to FIG. 2 a detailed block diagram of a single intra-oral on/off switching means such as 14 is shown. As shown in FIG. 2 each intra-oral on/off switching means such as 14 includes tongue-activated contacts 13 which are directly coupled to the on-board power supply 18. Lingual activation of the contacts 13 enables a control means 15. The control means 15 is coupled to a demand power supply 17 and also to a transmitter enabling means 21. The demand power supply 17 is, in turn, coupled to a modulator unit 19 which generates a first low frequency modulating signal. In accordance with an important aspect of the present invention, activation of the contacts 13 enables the control means 15. The control means 15 includes a timing circuit which begins to operate immediately after the contacts 13 are touched with the tongue. Only when the tongue is in contact with the contacts 13 for a period of time sufficient to indicate that activation of the contacts 13 is not inadvertent is the transmitter 22 enabled by the transmitter enabling means 21. Moreover, the transmitter is enabled only for a short, predetermined time period. These features are important in minimizing the power drain on the power supply 18 and will become clearer by reference to the detailed circuit diagram of the intra-oral control unit 14 which is shown in FIG. 3.

Figure 3:
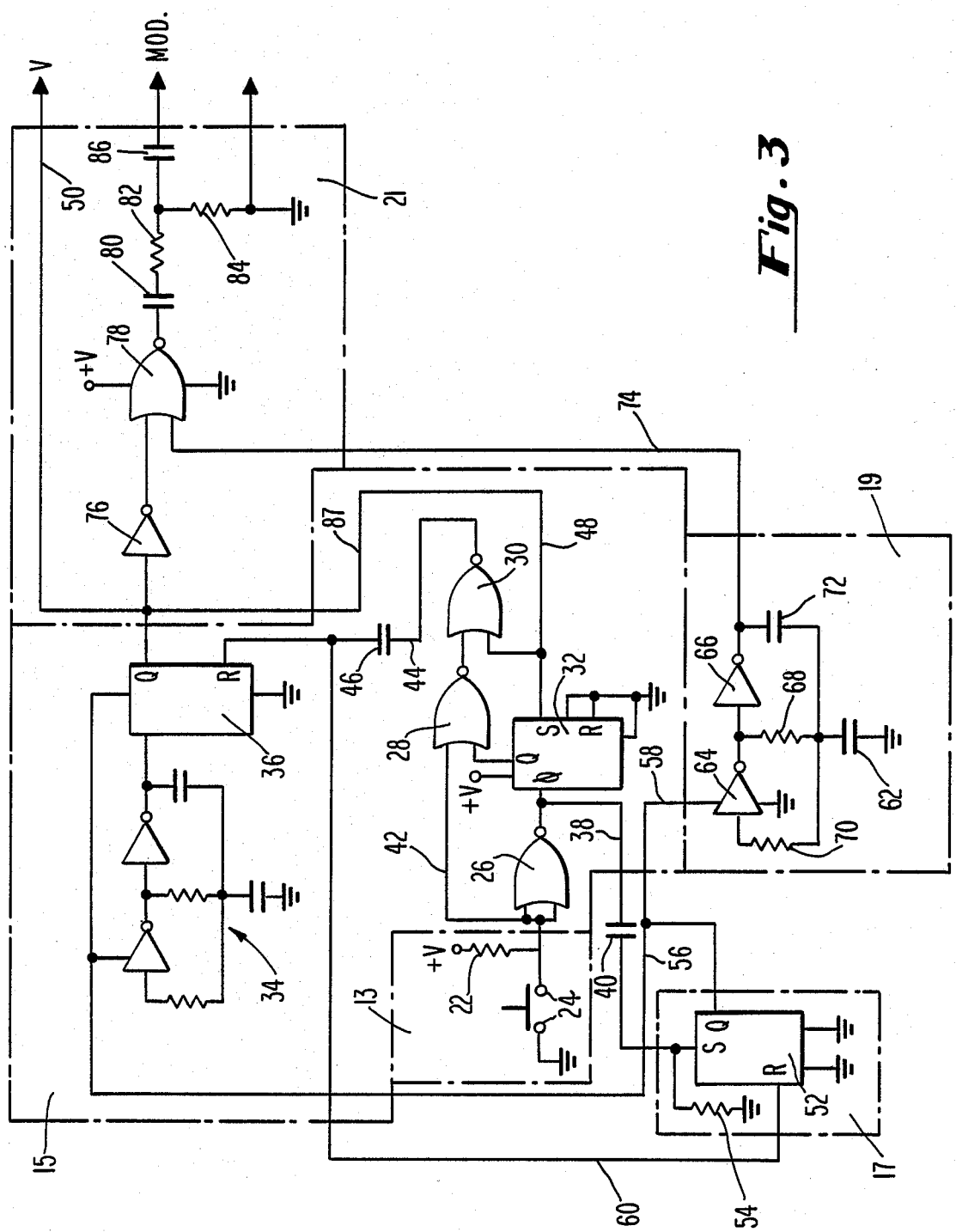
FIG. 3 is a schematic circuit diagram of the on/off switch of FIG. 2.

Referring now to FIG. 3 the details of the tongue-activated contacts 13, the control means 15, the demand power supply 17, the modulator unit 19 and the transmitter enabling means 21 will be seen.

As shown in FIG. 3, the tongue-activated contacts 13 are coupled to ground and also to a source of positive voltage provided from the on-board power supply 18 through a resistor 22. When the tongue enables the switch 24 the control means 15 is activated.

In accordance with the embodiment of FIG. 3, the control means 15 includes a control portion and a timing portion. The control portion of the control means 15 is comprised of a series of nor gates 26, 28 and 30 as well as a flip-flop 32. The timing portion is comprised of an astable multivibrator 34 and a counter.

Input to the control means 15 from the tongue contact 13 is received by nor gates 26 and 28. The output of nor gate 26 is coupled along line 38 through the capacitor 40 to the demand power supply 17 to enable the demand power supply. The output of the nor gate 26 is further supplied to the clock input of the flip-flop 32. When the voltage input to the nor gate 26 goes low, the demand power supply 17 is enabled. At the same time, the Q output of flip-flop 32 goes low, the output of nor gate 28 goes high and the output of nor gate 30 goes low.

From the foregoing description, it should be seen that when the tongue enables the switch 24, the demand power supply 17 is also enabled. In turn, the demand power supply 17 enables both the timing portion of the control means 15 and the modulator 19 in a manner which will now be described.

The demand power supply 17 as shown in FIG. 3 includes a flip-flop 52. The set input to the flip-flop 52 is coupled to ground via resistor 54 and is further coupled to the control means 15 via capacitor 40 on line 38. The Q output of the flip-flop 52 is coupled via line 56 to the astable multivibrator 34 as well as to the counter 36 of the timer portion of the control means 15. The Q output is further coupled via line 58 to the modulator unit 19. The reset output of the flip-flop 52 is coupled via line 60 to the output of nor gate 30. When the tongue enables the switch 24 of the tongue-activated contact 13, the demand power supply 17 has the effect of enabling the astable multivibrator 34 of the timing control means 15 and also of enabling a second astable multivibrator of the modulator unit 19.

The modulator unit 19, as mentioned above, includes an astable multivibrator which is comprised of inverters 64 and 66. The output of inverter 64 is directed back to the input of that inverter through resistors 68 and 70 as shown. The output of inverter 64 is also directed to the input of inverter 66 with feedback being provided from the output thereof through capacitor 72 and resistor 68. The output of the inverter 66 is further coupled to the transmitter enabling unit 21 along line 74. The astable multivibrator is coupled to ground by capacitor 62.

The transmitter enabling unit 21 is comprised of inverter 76, a nor gate 78 and an RC output network. The inverter 76 is coupled between the Q output of the counter 36 of the timing portion of the control means 15 and one input of the nor gate 78. The other input of nor gate 78 is provided from the modulator unit 19. The output of the nor gate 78 is directed through an RC network to the transmitter 22. The RC network comprises a series combination of capacitor 80 and resistor 82. Resistor 82 is coupled to ground via resistor 84 and coupled to the transmitter 22 via capacitor 86.

In operation, the transmitter enable circuit 21 shown in FIG. 3 transmits a positive voltage signal (V) along line 50 to the transmitter 22 when the counter 36 reaches a predetermined count and the Q output of the capacitor goes high. At the same time, the low frequency modulating signal (MOD) from the modulator 19 is passed via nor gate 78 and directed to the transmitter 22. The Q output of the counter is also directed along line 87 to nor gate 30 and to the set input of flip-flop 32 which, in turn, resets both the counter 36 and flip-flop 52.

Figure 4:
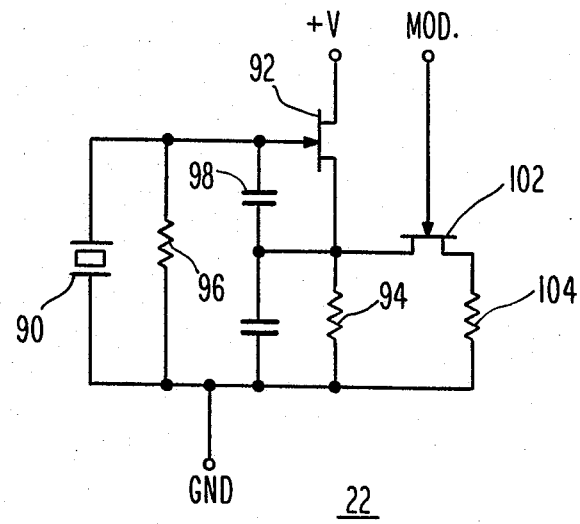
FIG. 4 is a schematic circuit diagram of an intra-oral transmitter which is particularly preferred for the practice of the present invention.

Referring now to FIG. 4, further details of the transmitter 22 will be seen. It has been found that the transmitter 22 shown in FIG. 4 is particularly suitable for accurate transmission from the intra-oral cavity. The circuit shown in FIG. 4 is a modified Colpitts oscillator circuit which includes a relatively high frequency crystal oscillating means 90. This crystal oscillating means generates a relatively high frequency carrier signal, for example, 145 MHz. The crystal oscillating means is coupled to the gate of a first FET 92. FET 92 is also coupled between the voltage source (V) from the transmitter enabling unit 21 and ground through resistor 94 and capacitor 100. Coupled between the gate of the FET 92 and ground is a network which includes the aforementioned crystal oscillator 90 in parallel with a resistor 96 and further in parallel with capacitors 98 and 100. The low frequency modulating signal (MOD) from the transmitter enabling means 21 is coupled to the gate of a second field effect transistor 102 coupled between the output of the first FET 92 and ground through resistor 104.

While the present invention has been described in connection with an intra-oral control unit and system useful for quadriplegics, it may also find utility in other fields, for example, in the control of complex machinery by workers or operators whose hands are otherwise occupied. Thus, while a particular embodiment of the present invention has been shown and described, it will, of course, be appreciated that various modifications may be made without departing from the principles of the invention. The appended claims are, therefore, intended to cover any such modifications within the true spirit and scope of the invention.

What is claimed is:

1. An environmental control unit comprising:
   an intra-oral power supply;
   at least one intra-oral lingually operated switching means, said switching means including
   a control means including a timing portion;
   a demand power supply;
   a first oscillating means, responsive to said demand power supply, for generating a first relatively low frequency modulating signal; and
   transmitter enabling means, responsive to both said control means and to said first oscillating means for outputting said modulating signal if said switching means has been continuously activated for a predetermined time; and;
   an intra-oral transmitter responsive to said switching means and to said modulating signal for transmitting control signals from the intra-oral cavity of a patient to a position external to said patient.

2. The environmental control unit of claim 1 in which said transmitter comprises:
   a second oscillating means for generating a relatively high frequency carrier signal and for frequency modulating said first low frequency modulating signal upon said carrier signal to produce a first control signal.

3. The environmental control unit of claim 2 wherein said first oscillating means comprises:
   an astable multivibrator.

4. The environmental control unit of claim 2 wherein said second oscillating means comprises a crystal controlled oscillator circuit.

5. An environmental control system adapted for use by a plurality of quadriplegic patients comprising:
   an environmental control unit for each patient in said plurality, each said unit including:
   an intra-oral power supply;
   at least one intra-oral lingually operated switching means, said switching means including a control means having a timing portion;
   a demand power supply;
   a first oscillating means, responsive to said demand power supply, for generating a relatively low frequency modulating signal;
   transmitter enabling means, responsive to both said control means and to said oscillating means for outputting said modulating signal if said switching means has been continuously activated for a predetermined time;
   an intra-oral transmitter responsive to said switching means and to said power supply for transmitting control signals uniquely identifying a particular one of said plurality of patients upon lingual activation of said switching means by that patient;
   an external receiver responsive to the control signals emitted by each intra-oral transmitter; and
   a controller responsive to said receiver for generating output signals for each patient in said group.

6. The environmental control system of claim 5 in which, for each environmental control unit, said intra-oral transmitter comprises:
   a second oscillating means for generating a relatively high frequency carrier signal and for frequency modulating said first low frequency signal upon said carrier signal to produce a first control signal.

* * * * *